United States Patent
Cai et al.

(10) Patent No.: US 10,598,652 B2
(45) Date of Patent: Mar. 24, 2020

(54) METHODS OF DIAGNOSING POST-OPERATIVE COMPLICATIONS USING SERUM NITRIC OXIDE LEVELS

(71) Applicant: The Regents of the University of California, Oakland, CA (US)

(72) Inventors: Hua Cai, Los Angeles, CA (US); Kimberly Howard-Quijano, Los Angeles, CA (US); Aman Mahajan, Sherman Oaks, CA (US); Ji Youn Youn, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 72 days.

(21) Appl. No.: 15/564,820

(22) PCT Filed: Apr. 8, 2016

(86) PCT No.: PCT/US2016/026590
§ 371 (c)(1),
(2) Date: Oct. 6, 2017

(87) PCT Pub. No.: WO2016/164687
PCT Pub. Date: Oct. 13, 2016

(65) Prior Publication Data
US 2018/0113112 A1    Apr. 26, 2018

Related U.S. Application Data

(60) Provisional application No. 62/145,449, filed on Apr. 9, 2015.

(51) Int. Cl.
*G01N 33/49* (2006.01)
*C01B 21/24* (2006.01)
*A61B 5/145* (2006.01)
*A61B 5/00* (2006.01)

(52) U.S. Cl.
CPC ......... *G01N 33/4925* (2013.01); *A61B 5/145* (2013.01); *C01B 21/24* (2013.01); *A61B 5/7275* (2013.01); *G01N 2800/326* (2013.01); *G01N 2800/50* (2013.01); *G01N 2800/7009* (2013.01)

(58) Field of Classification Search
CPC ......... G01N 2800/326; G01N 2800/50; G01N 2800/52; G01N 2800/7009; G01N 33/4925; A61B 5/145; A61B 5/7275
See application file for complete search history.

(56) References Cited

U.S. PATENT DOCUMENTS

2014/0187652 A1*  7/2014  Heudig .............. G01N 33/6893
                                                              514/789

FOREIGN PATENT DOCUMENTS

| CN | 103946709 A | 7/2014 |
| WO | 2013034264 A1 | 3/2013 |
| WO | 2013098294 A1 | 7/2013 |

OTHER PUBLICATIONS

Anselmi, Amedeo et al. "Postoperative inflammatory reaction and atrial fibrillation: Simple correlation or causation?" Ann. Thorac. Surg. (2009) 88 326-33. (Year: 2009).*
Mian, Asad I. et al. "Nitric oxide and its metabolites in the critical phase of illness: Rapid biomarkers in the making." The Open Biochemistry Journal (2013) 7 24-32. (Year: 2013).*
International Search Report received in PCT/US2016/026590 dated Jul. 12, 2016.
Written Opinion received in PCT/US2016/026590 dated Jul. 12, 2016.
Cai, et al., "Downregulation of Endocardial Nitric Oxide Synthase Expression and Nitric Oxide Production in Atrial Fibrillation: Potential Mechanisms for Atrial Thrombosis and Stroke", Nov. 11, 2002, pp. 2854-2858, vol. 106, No. 22, Publisher: Circulation.
Ratajczak-Wrona, et al., "Levels of biological markers of nitric oxide in serum of patients with squamous cell carcinoma of the oral cavity", Sep. 1, 2013, pp. 141-145, vol. 5, No. 3, Publisher: International Journal of Oral Science.
Uysal, et al., "Perioperative High-Dose Amiodarone Elevates Nitric Oxide Levels in Patients Undergoing Coronary Artery Bypass Surgery", Jan. 1, 2013, pp. 486-492, vol. 24, No. 4, Publisher: Biomedical Research India.
First Office Action and Search Report received in CN2016800209048 dated Nov. 26, 2019.

* cited by examiner

*Primary Examiner* — Christopher Adam Hixson
(74) *Attorney, Agent, or Firm* — Suzannah K. Sundby, Esq.; Canady + Lortz LLP (57) ABSTRACT

Disclosed herein are methods of using serum nitric oxide levels to diagnose subjects as having or likely to develop a post-operative complication.

16 Claims, 8 Drawing Sheets

METHODS OF DIAGNOSING POST-OPERATIVE COMPLICATIONS USING SERUM NITRIC OXIDE LEVELS

ACKNOWLEDGEMENT OF GOVERNMENT SUPPORT

This invention was made with Government support under HL119968, awarded by the National Institutes of Health. The Government has certain rights in the invention.

BACKGROUND OF THE INVENTION

Cardiac surgery with cardiopulmonary bypass (CPB) is associated with a systemic inflammatory response, increase in oxidative stress, and upregulation of inflammatory mediators including C-reactive protein (CRP), interleukin 6 (IL-6), and B-type natriuretic peptide (BNP). Increased systemic inflammation is a risk factor for worse post-operative (postop) outcomes including the development of acute kidney injury (AKI) and atrial fibrillation (AF). It has been shown that inflammation induced oxidative stress leads to reduced nitric oxide (NO) bioavailability and concentration in tissues. See Cai, et al. (2002) Circulation 106:2854-2858 (NO measured in left atrial and aortic samples in a porcine model of AF). Unfortunately, measuring NO in tissues require invasive tissue biopsies, which may increase the risk of postop complications, or may only be performed postmortem.

Thus, a need exists for methods for screening and monitoring postop complications such as systemic inflammation, and development of postop AF and AKI, which are particularly prevalent in surgical patients having high morbidity and/or high mortality, in subjects without further increasing their risk of postop complications.

SUMMARY OF THE INVENTION

In some embodiments, the present invention provides a method of diagnosing a subject as having or likely to develop a postoperative complication after an operation, which comprises measuring the concentration of serum nitric oxide in a first blood sample obtained from the subject before the operation; measuring the concentration of serum nitric oxide in a second blood sample obtained from the subject at about 24 hours after the operation; calculating the percent decrease of serum nitric oxide concentration from the concentration of serum nitric oxide in the first blood sample to the concentration of the serum nitric oxide in the second blood sample; and diagnosing the subject as having or likely to develop the postoperative complication where the percent decrease of the serum nitric oxide concentration is at least about 40%, about 40%, about 40-45%, about 40-50%, about 45-50%, or about 55-60%. In some embodiments, the method further comprises diagnosing the subject as having or likely to develop atrial fibrillation where the percent decrease of the serum nitric oxide concentration is at least about 40%, about 40%, about 40-45%, about 40-50%, about 45-50%. In some embodiments, the method further comprises diagnosing the subject as having or likely to develop acute kidney injury where the percent decrease of the serum nitric oxide concentration is about 55-60%. In some embodiments, the methods further comprise treating the subject for the postoperative complication where the subject is diagnosed as having the postoperative complication. In some embodiments, the methods exclude treating the subject for the postoperative complication where the subject is diagnosed as not having or not likely to develop the postoperative complication.

In some embodiments, the present invention provides a method of diagnosing a subject as having or likely to develop a postoperative complication after an operation, which comprises measuring the concentration of serum nitric oxide in a first blood sample obtained from the subject before the operation; measuring the concentration of serum nitric oxide in a second blood sample obtained from the subject at about 24 hours after the operation; calculating the percent decrease of serum nitric oxide concentration from the concentration of serum nitric oxide in the first blood sample to the concentration of the serum nitric oxide in the second blood sample; and diagnosing the subject as having or likely to develop the postoperative complication where the percent decrease of the serum nitric oxide concentration is at least about 28% more, about 28% more, about 28-53% more, about 28-58% more, about 53-58% more, or about 64-67% more than the average percent decrease exhibited by normal control subjects. In some embodiments, the method further comprises diagnosing the subject as having or likely to develop atrial fibrillation where the percent decrease of the serum nitric oxide concentration is at least about 28% more, about 28% more, about 28-53% more, about 28-58% more, about 53-58% more than the average percent decrease exhibited by normal control subjects. In some embodiments, the method further comprises diagnosing the subject as having or likely to develop acute kidney injury where the percent decrease of the serum nitric oxide concentration is about 64-67% more than the average percent decrease exhibited by normal control subjects. In some embodiments, the methods further comprise treating the subject for the postoperative complication where the subject is diagnosed as having or likely to develop the postoperative complication. In some embodiments, the methods exclude treating the subject for the postoperative complication where the subject is diagnosed as not having or not likely to develop the postoperative complication.

In some embodiments, the present invention provides a method of characterizing a postop blood sample as being from a subject who has or is likely to have a postoperative complication after an operation, said postop blood sample being obtained from the subject about 24 hours after the operation, which comprises measuring the concentration of serum nitric oxide in the postop blood sample and calculating the percent decrease in serum nitric oxide concentration from the concentration of serum nitric oxide in a preop blood sample obtained from the subject before the operation, and characterizing the postop blood sample as being from a subject who has or is likely to develop the postoperative complication where (a) the percent decrease of the serum nitric oxide concentration is at least about 40%, about 40%, about 40-45%, about 40-50%, about 45-50%, or about 55-60%, or (b) the percent decrease of the serum nitric oxide concentration is at least about 28% more, about 28% more, about 28-53% more, about 28-58% more, about 53-58% more, or about 64-67% more than the average percent decrease exhibited by normal control subjects. In some embodiments, the method further comprises categorizing the postop blood sample as being from a subject who has or is likely to develop atrial fibrillation where the percent decrease of the serum nitric oxide concentration is at least about 40%, about 40%, about 40-45%, about 40-50%, about 45-50%. In some embodiments, the method further comprises characterizing the postop blood sample as being from a subject who has or is likely to develop acute kidney injury where the percent decrease of the serum nitric oxide concentration is about 55-60%. In some embodiments, the method further comprises characterizing the postop blood sample as being from a subject who has or is likely to develop atrial fibrillation where the percent decrease of the serum nitric oxide concentration is at least about 28% more, about 28% more, about 28-53% more, about 28-58% more, about 53-58% more than the average percent decrease exhibited by normal control subjects. In some embodiments, the method further comprises characterizing the postop blood sample as being from a subject who has or is likely to develop acute kidney injury where the percent decrease of the serum nitric oxide concentration is about 64-67% more than the average percent decrease exhibited by normal control subjects. In some embodiments, the method further comprises measuring the serum nitric oxide concentration in the preop blood sample.

In some embodiments of these methods, the blood samples are plasma samples. In some embodiments of these methods, the concentrations of serum nitric oxide in the blood samples are measured using a detectable label added thereto. In some embodiments of these methods, the operation is cardiac surgery. In some embodiments of these methods, the operation is cardiac surgery with cardiopulmonary bypass.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIGS. 1A-1C show the change in circulating inflammatory markers following cardiac surgery with cardiopulmonary bypass. FIG. 1C is a graph showing the postop change in C-reactive protein (CRP). Circulating NO dropped significantly at 24 hour postop, which is the time frame when postop AF develops most frequently. Following the drop in NO, BNP, and CRP levels went up, indicating persistent inflammatory activation *=p<0.001.

FIGS. 5A-5C show the median serum NO, B-type Natriuretic Peptide (BNP), and interleukin-6 (IL-6) baseline levels (Preop) as compared to 24, 48, and 72 hours following cardiac surgery with cardiopulmonary bypass (24 hr postop, 48 hr postop, and 72 hr postop).

DETAILED DESCRIPTION OF THE INVENTION

As disclosed herein, inflammation following cardiac surgery with cardiopulmonary bypass (CPB) decreases serum nitric oxide (NO) level, and this reduction in NO bioavailability can be a risk factor for development of postoperative complications including acute kidney injury (AKI) and atrial fibrillation (AF).

Figure 5A:
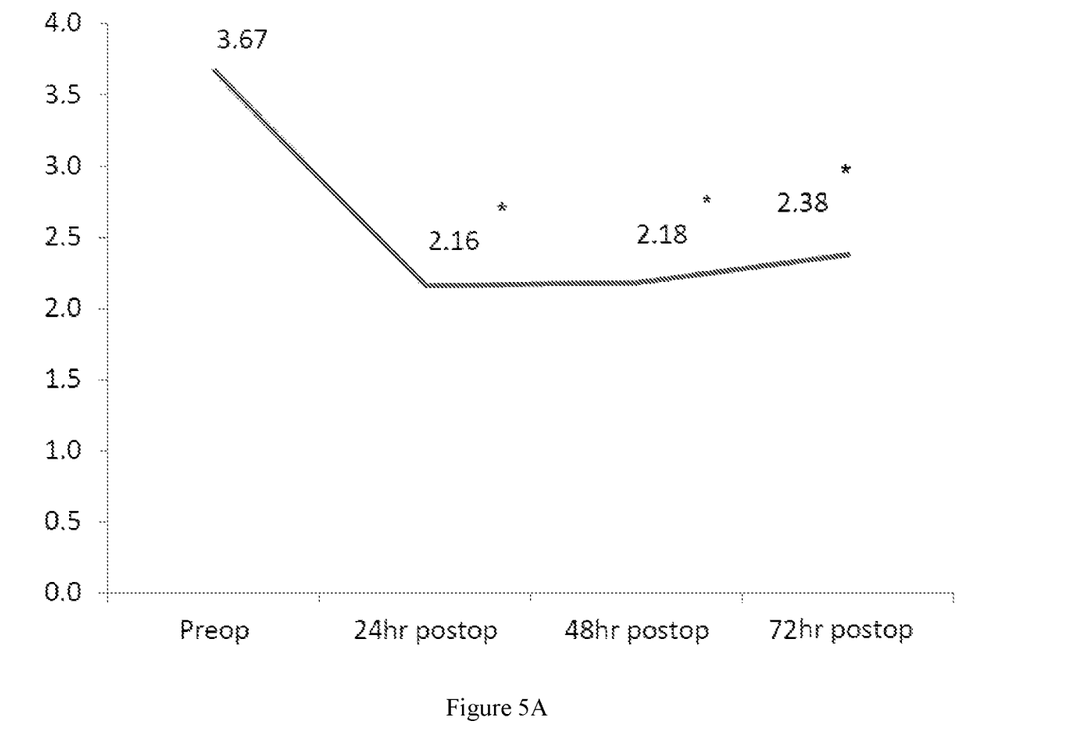
FIG. 5A is a graph showing the postop change in serum nitric oxide (NO) levels.
Figure 5B:
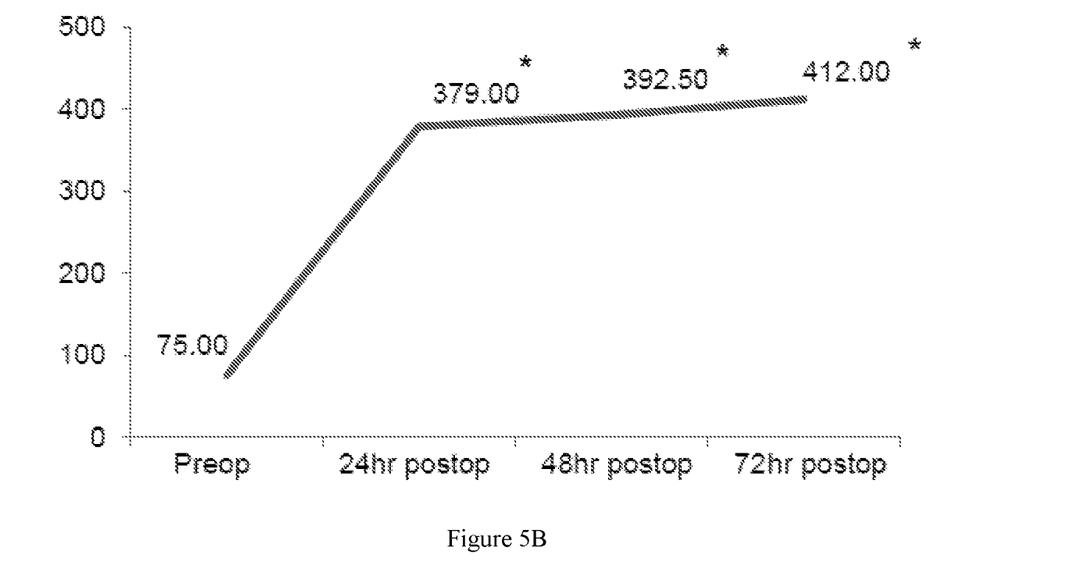
FIG. 5B is a graph showing the postop change in B-type natriuretic peptide (BNP).
Figure 5C:
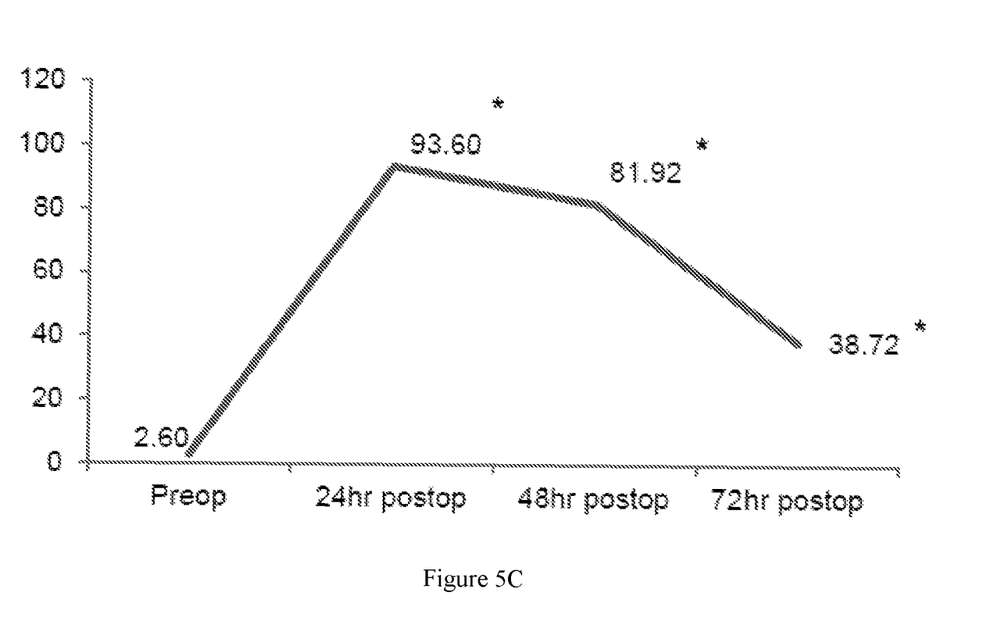
FIG. 5C is a graph showing the postop change in interleukin-6 (IL-6). Levels are in μM. *p<0.001, n=111.
Figure 6:
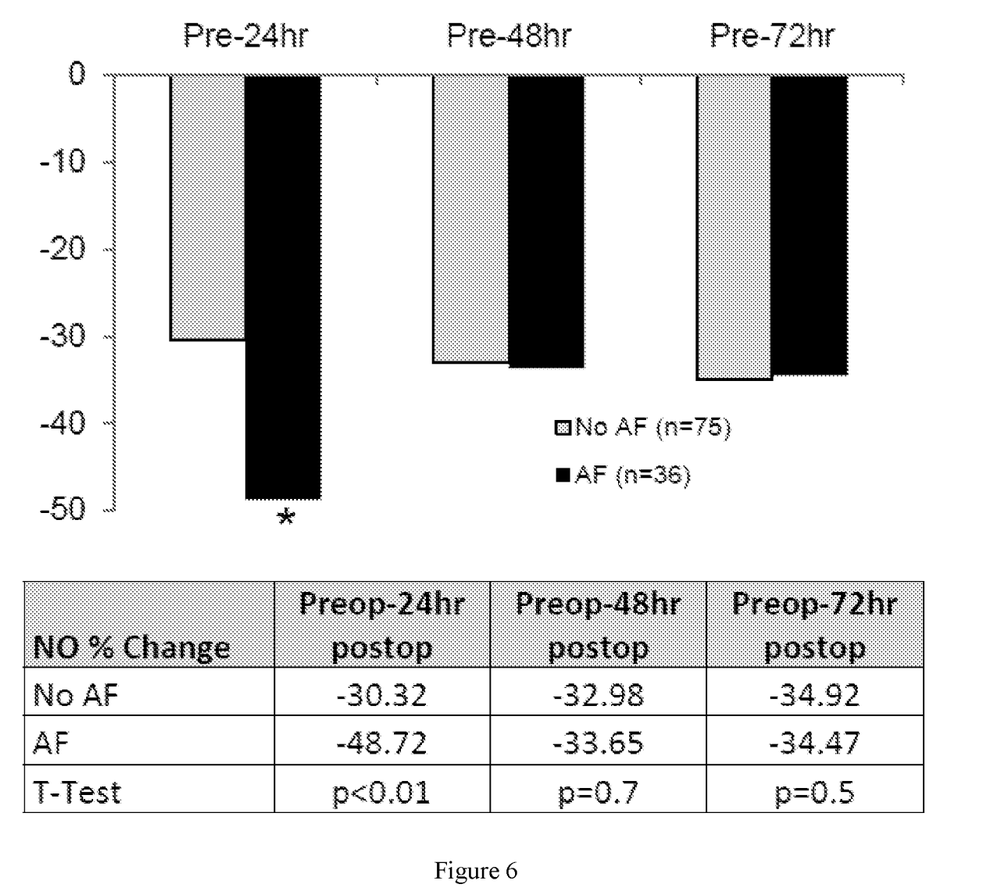
FIG. 6 is a graph showing the serum NO % change in subjects with and without AF. All subjects, n=111, Postop AF, n=36 (33%), Without AF, n=75.

As disclosed herein, there is a decrease in serum NO following cardiac surgery, representing reduced bioavailability likely due to a systemic inflammatory response induced by CPB. This reduction in circulating NO is observed prior to the peaks of B-type natriuretic peptide (BNP) and C-reactive protein (CRP) levels (FIGS. 1A-1C) and prior to the peaks of BNP and interleukin-6 (IL-6) (FIGS. 5A-5C). Thus, serum NO levels can be used to detect postoperative systemic inflammation before other inflammatory biomarkers are observed. The experimental data also indicate that while reduced serum NO levels may be caused by initial inflammation resulting from surgery, the serum NO levels might activate feed-forward mechanisms that sustain inflammatory responses, such as those with elevated BNP and CRP levels. The experiments herein show that patients who developed AKI or AF have a larger decrease from baseline in serum NO levels, at 24 hours postop compared to those who did not develop AKI or AF (FIGS. 2A-2B, FIG. 3, and FIG. 6). Therefore, serum NO levels may be used to diagnosis, monitor, and/or treat postoperative complications following, for example, cardiac surgery with cardiopulmonary bypass.

Specifically, as disclosed herein, subjects who developed AKI exhibited about a 55-60% decrease in serum NO at 24 hours postop whereas subjects who did not develop AKI exhibited only about a 33-36% decrease in serum NO at 24 hours postop. Similarly, of the 47, 64, and 75 patient sample sizes, subjects who developed AF exhibited about a 40-45% decrease in serum NO at 24 hours postop, whereas subjects who did not develop AF exhibited only about a 27-33% decrease in serum NO at 24 hours postop. Of the 111 patient sample size, subjects who developed AF exhibited about a 49% decrease in serum NO 24 hours postop and subjects who did not develop AF exhibited only about a 31% decrease in serum NO 24 hours postop.

Therefore, in some embodiments, the present invention is directed to a method of diagnosing a subject as having or likely to develop a postoperative complication after an operation which comprises diagnosing the subject as having or likely to develop a postoperative complication where the subject's serum NO at 24 hours postop is at least about 40% less than the subject's serum NO prior to the operation. In some embodiments, the present invention is directed to a method of diagnosing a subject as having or likely to develop a postoperative complication after an operation which comprises diagnosing the subject as having or likely to develop a postoperative complication where the subject's serum NO at 24 hours postop is about 40-45% less than the subject's serum NO prior to the operation. In some embodiments, the present invention is directed to a method of diagnosing a subject as having or likely to develop a postoperative complication after an operation which comprises diagnosing the subject as having or likely to develop a postoperative complication where the subject's serum NO at 24 hours postop is about 40-50% less than the subject's serum NO prior to the operation. In some embodiments, the present invention is directed to a method of diagnosing a subject as having or likely to develop a postoperative complication after an operation which comprises diagnosing the subject as having or likely to develop a postoperative complication where the subject's serum NO at 24 hours postop is about 55-60% less than the subject's serum NO prior to the operation. In some embodiments, where the subject's serum NO is about 40-45% less than the subject's serum NO prior to the operation, the subject is diagnosed as having or likely to develop AF as the postoperative complication. In some embodiments, where the subject's serum NO is about 40-50% less than the subject's serum NO prior to the operation, the subject is diagnosed as having or likely to develop AF as the postoperative complication. In some embodiments, where the subject's serum NO is about 55-60% less than the subject's serum NO prior to the operation, the subject is diagnosed as having or likely to develop AKI as the postoperative complication. In some embodiments, the operation is cardiac surgery. In some embodiments, the operation is cardiac surgery with CPB. In some embodiments, the method comprises obtaining a blood sample from the subject and measuring the amount of NO in the sample using a detectable label added thereto. In some embodiments, the method comprises calculating the difference between the amount of serum NO in a first blood sample obtained from the subject before the operation and the amount of serum NO in a second blood sample obtained from the subject about 24 hours after the operation. In some embodiments, the blood sample is a serum sample.

As disclosed herein, at 24 hours after an operation, subjects who developed AKI exhibited a negative change in serum NO that was about 64-67% more than that of subjects who did not develop AKI. Similarly, at 24 hours after an operation, subjects who developed AF exhibited a negative change in serum NO that was about 28-53% (in the 47, 64, and 75 patient sample sizes) and about 58% (in the 111 patient sample size) more than that of subjects who did not develop AF.

Therefore, in some embodiments, the present invention is directed to a method of diagnosing a subject as having or likely to develop a postoperative complication after an operation which comprises diagnosing the subject as having or likely to develop a postoperative complication where, at 24 hours postop, the subject exhibits a negative change in serum NO that is at least about 28% more than that of a normal control (e.g., the average negative change in serum NO at 24 hours postop from a pool of subjects who did not develop a postoperative complication). In some embodiments, the present invention is directed to a method of diagnosing a subject as having or likely to develop a postoperative complication after an operation which comprises diagnosing the subject as having or likely to develop a postoperative complication where, at 24 hours postop, the subject exhibits a negative change in serum NO that is about 28-53% more or about 28-58% more than that of a normal control. In some embodiments, the present invention is directed to a method of diagnosing a subject as having or likely to develop a postoperative complication after an operation which comprises diagnosing the subject as having or likely to develop a postoperative complication where, at 24 hours postop, the subject exhibits a negative change in serum NO that is about 64-67% more than that of a normal control. In some embodiments, where the subject's serum NO is about 28-53% more or about 28-58% more than that of a normal control, the subject is diagnosed as having or likely to develop AF as the postoperative complication. In some embodiments, where the subject's serum NO is about 64-67% more than that of a normal control, the subject is diagnosed as having or likely to develop AKI as the postoperative complication. In some embodiments, the operation is cardiac surgery. In some embodiments, the operation is cardiac surgery with CPB. In some embodiments, the method comprises obtaining a blood sample from the subject and measuring the amount of NO in the sample using a detectable label added thereto. In some embodiments, the method comprises calculating the difference between the amount of serum NO in a first blood sample obtained from the subject before the operation and the amount of serum NO in a second blood sample obtained from the subject about 24 hours after the operation. In some embodiments, the blood sample is a serum sample.

In some embodiments, the methods further comprise, after diagnosing the subject as having or likely to develop the postoperative complication, treating the subject for the postoperative complication. For example, if a subject is determined to have a likelihood of developing AF as a postop complication, the subject may be administered one or more pharmacologic agents, such as amiodarone, colchicine, beta-blockers, and the like, which are known or used to prevent or treat AF before AF occurs. Alternatively or in addition to treatment with one or more pharmacologic agents, the subject may be subjected to atrial pacing protocols. If a subject is determined to have a likelihood of developing AKI as a postop complication, the subject may be treated with optimization of fluid status and correction of volume deficits to maintain a mean blood pressure of >65 mmHg and central venous pressure of >8-12 mmHg and/or by reducing dosage or replacing nephrotoxic medications postoperatively to prevent or treat AKI before AKI occurs.

The following examples are intended to illustrate but not to limit the invention.

Initial Studies

Prospectively enrolled 64 consecutive adult patients undergoing cardiac surgery with CPB were evaluated. Patients with end stage renal disease on hemodialysis, and patients with 1 or more episodes of AF 30 days preoperatively were excluded. Peripheral blood samples were drawn at 4 time points: preoperatively, and postoperatively at 24, 48, and 72 hours. CRP, IL-6, and BNP were measured in blood samples using methods known in the art, and NO levels were measured using a Griess reaction for nitrite/nitrate assay. See Giustarini et al. "Nitrite and Nitrate Measurement by Griess Reagent in Human Plasma: Evaluation of Interferences and Standardization" Methods in Enzymology, 2008, Elsevier, Vol. 440, pp. 361-380, which is herein incorporated by reference in its entirety. In brief, 1 ml of plasma was incubated with 10 mg of protamine sulfate for 5 minutes at room temperature. After centrifugation at 10,000 rpm for 10 minutes, 150 µL of supernatant was mixed with equal volume of modified Griess reagent (Sigma) at room temperature for 5 minutes. Optical density at 540 nm was measured using a Bio-Tek Plate Reader®. Nitrate levels were calculated from a standard curve prepared with known concentrations of sodium nitrate (0-10

μM). Calibration of the assay was performed using mouse serum and then optimized for human serum testing.

Postop outcomes included length of hospital stay, AKI defined by the Acute Kidney Injury Network criteria (see Mehta, et al. (2007) Crit Care 11:R31 (which is herein incorporated by reference in its entirety), and AF defined as an irregular rhythm with no discernible P waves lasting greater than 30 seconds.

Figure 1A:
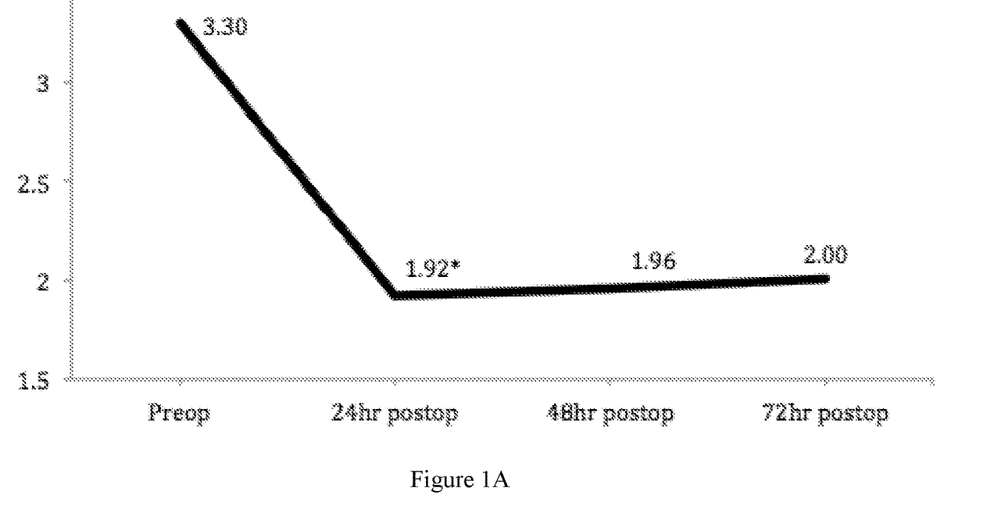
FIG. 1A is a graph showing the postop change in serum nitric oxide (NO) levels.
Figure 1B:
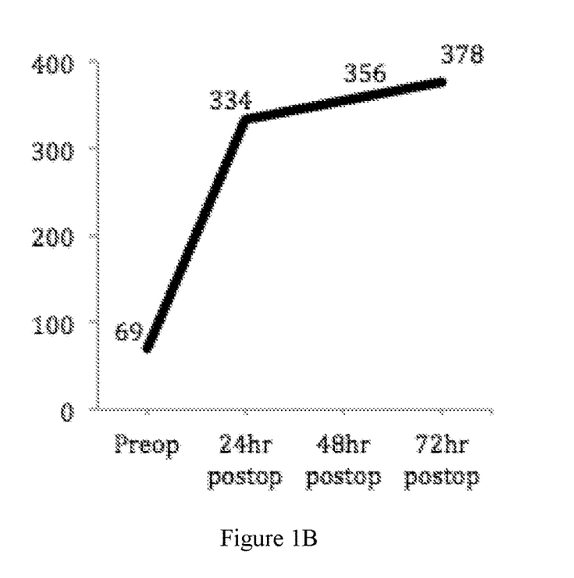
FIG. 1B is a graph showing the postop change in B-type natriuretic peptide (BNP).
Figure 1C:
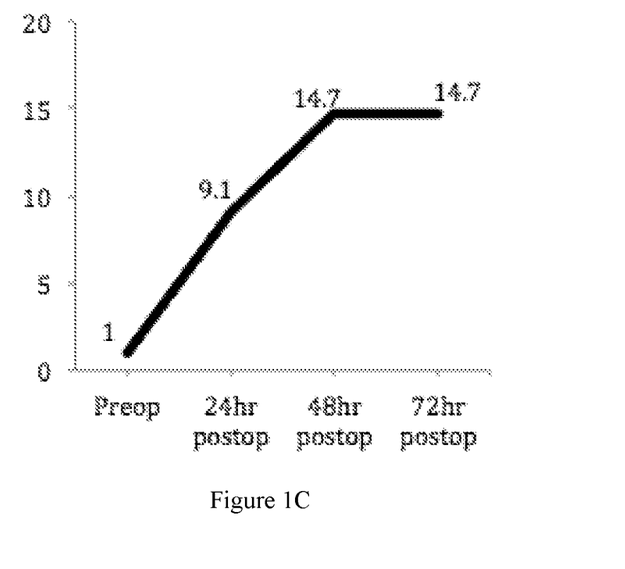
Figure 2A:
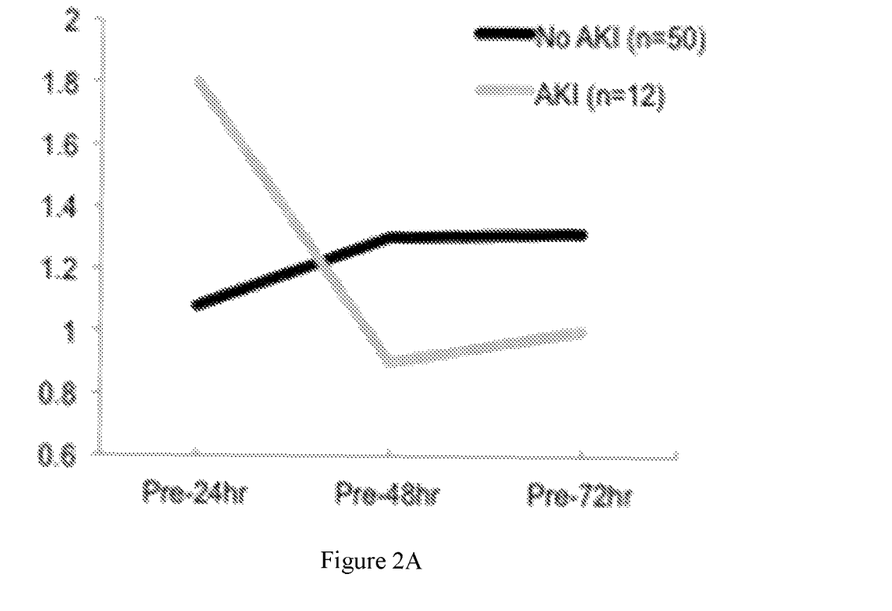
FIGS. 2A-2B show changes in serum NO levels in patients with/without AKI (FIG. 2A) or AF (FIG. 2B); of note, changes in NO levels during the first 24 hours was clearly evident in patients with AF or AKI, but not in those without.
Figure 2B:
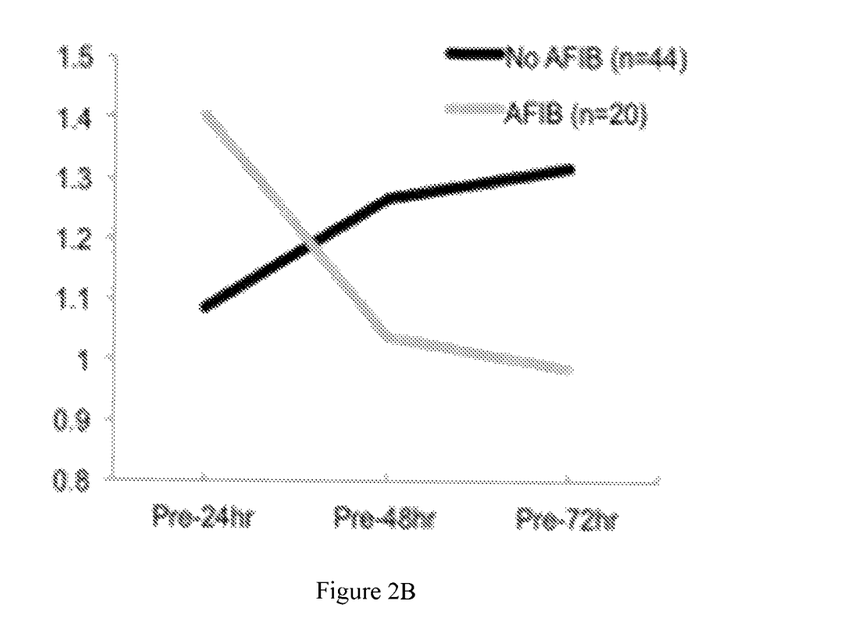
Figure 3:
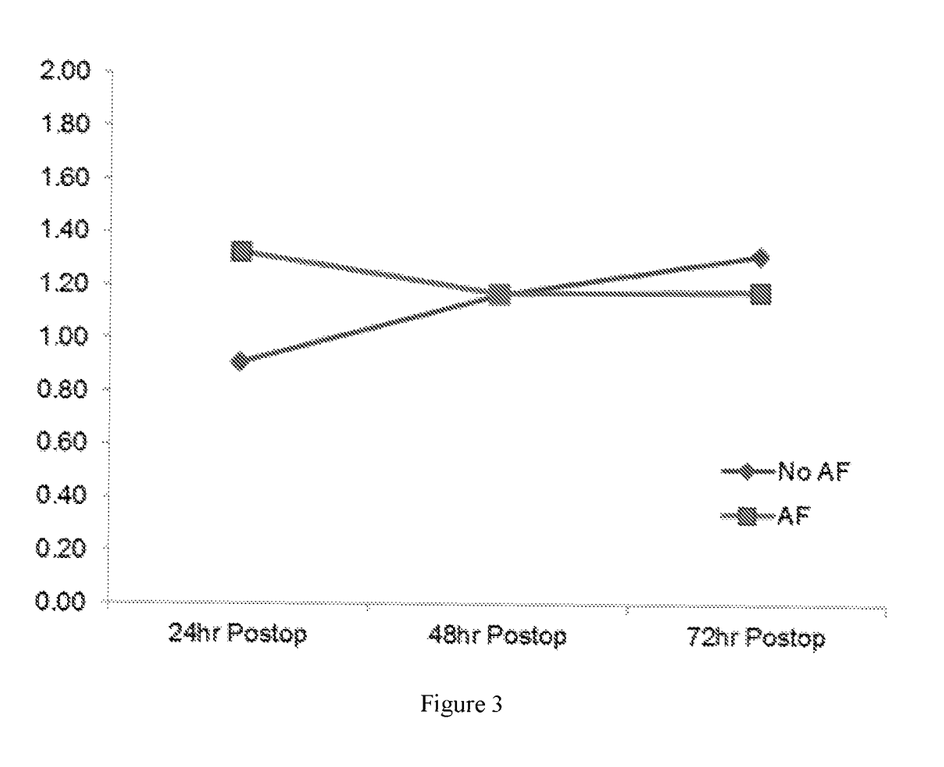
FIG. 3 is a graph showing the median change in serum NO levels from baseline preop to 24, 48, and 72 hours postop in patients with and without postoperative atrial fibrillation (AF). Patients who developed AF had larger decline in serum NO levels. All subjects, n=75.

A significant reduction in median serum NO levels was observed after cardiac surgery with CPB; from 3.30 μM preoperatively to a nadir of 1.92 μM (n=64, p<0.001) at 24 hours postop. The nadir of postop serum NO preceded the peak of median CRP and BNP (FIG. 1). There was a trend toward a larger decrease in serum NO at 24 hours postop in patients who developed AKI (n=12, delta NO=1.80 μM; no AKI: n=50, delta NO=1.08 μM) and AF (n=20, delta NO=1.40 μM; no AF: n=44, delta NO=1.09 μM). Thus, subjects who developed AKI exhibited about a 55% decrease in serum NO 24 hours postop and subjects who did not develop AKI exhibited only about a 33% decrease in serum NO 24 hours postop. Said another way, at 24 hours postop, subjects who developed AKI exhibit a negative change in serum NO that is about 67% more than that of subjects who do not develop AKI. Similarly, subjects who developed AF exhibited about a 42% decrease in serum NO 24 hours postop and subjects who did not develop AF exhibited only about a 33% decrease in serum NO 24 hours postop. In other words, at 24 hours postop, subjects who developed AF exhibit a negative change in serum NO that is about 28% more than that of subjects who do not develop AF.

This is consistent with results from 47 patients in which a significant reduction in median serum NO levels was observed after cardiac surgery with CPB; from 3.01 μM preoperatively to a nadir of 1.71 μM (n=47, p<0.001) at 24 hours postop. The nadir of postop serum NO preceded the peak of median CRP and BNP. There was a trend toward a larger decrease in serum NO at 24 hours postop in patients who developed AKI (n=11, delta NO=1.77 μM; no AKI: n=36, delta NO=1.08 μM) and AF (n=13, delta NO=1.32 μM; no AF: n=34, delta NO=0.86 μM). Thus, subjects who developed AKI exhibited about a 59% decrease in serum NO 24 hours postop and subjects who did not develop AKI exhibited only about a 36% decrease in serum NO 24 hours postop. Said another way, at 24 hours postop, subjects who developed AKI exhibit a negative change in serum NO that is about 64% more than that of subjects who do not develop AKI. Similarly, subjects who developed AF exhibited about a 44% decrease in serum NO 24 hours postop and subjects who did not develop AF exhibited only about a 29% decrease in serum NO 24 hours postop. In other words, at 24 hours postop, subjects who developed AF exhibit a negative change in serum NO that is about 53% more than that of subjects who do not develop AF.

Further Studies

In further studies, 75 consecutive adult patients undergoing cardiac surgery with CPB were enrolled and evaluated as above.

Figure 4:
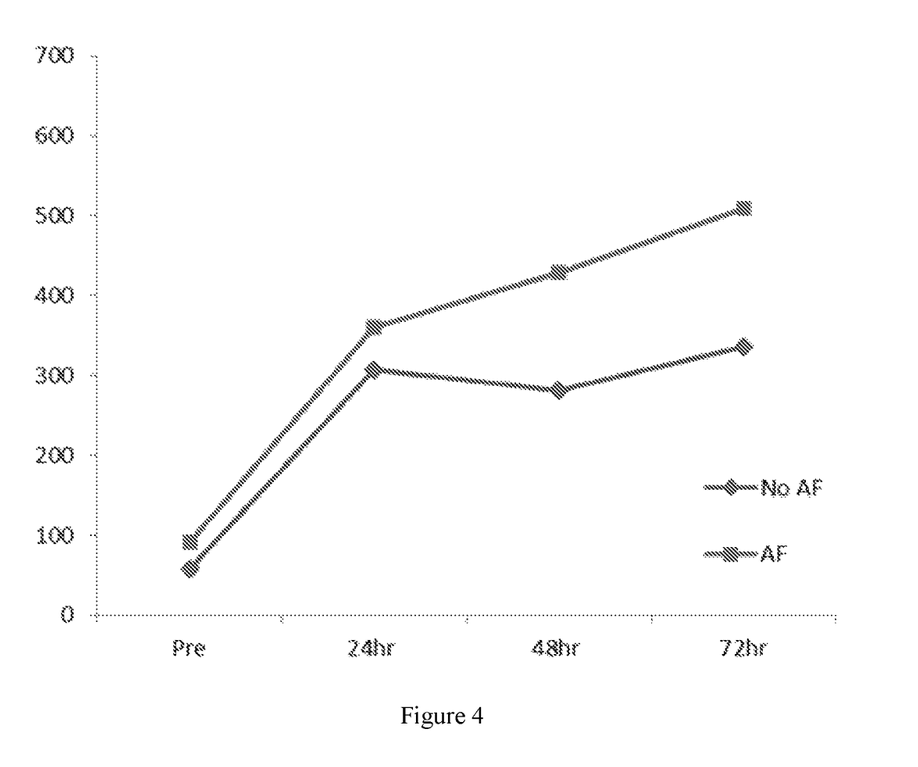
FIG. 4 is a graph showing the median serum B-type natriuretic peptide (BNP) levels pre- and postop (24 hr, 48 hr, and 72 hr) in patients with and without postoperative atrial fibrillation (AF). Patients with AF had higher BNP levels. All subjects, n=75.

A significant reduction in median serum NO levels was observed after cardiac surgery with CPB; from 3.34 μM preoperatively to a nadir of 1.96 μM (n=75, p<0.0001) at 24 hours post-op. The nadir of postop serum NO preceded the peak of median CRP and BNP (FIGS. 1 and 4). There was a trend toward a larger decrease in serum NO at 24 hours postop in patients who developed AF (n=23, delta NO=1.33 μM; no AF: n=52, delta NO=0.91 μM). Thus, subjects who developed AF exhibited about a 40% decrease in serum NO 24 hours postop and subjects who did not develop AF exhibited only about a 27% decrease in serum NO 24 hours postop. In other words, at 24 hours postop, subjects who developed AF exhibit a negative change in serum NO that is about 46% more than that of subjects who do not develop AF.

Additional Studies

In additional studies, 111 consecutive adult patients undergoing cardiac surgery with CPB were enrolled and evaluated as above.

A significant reduction in median serum NO levels was observed after cardiac surgery with CPB; from 3.67 μM preoperatively to a nadir of 2.16 μM (n=111, p<0.0001) at 24 hours postop. As before, the nadir of postop serum NO preceded the peak of median CRP (FIG. 5). There was a trend toward a larger decrease in serum NO at 24 hours postop in patients who developed AF (n=36, delta NO=1.33 μM; no AF: n=75, delta NO=0.9 μM). Thus, in this larger cohort, subjects who developed AF exhibited about a 49% decrease in serum NO 24 hours postop and subjects who did not develop AF exhibited only about a 31% decrease in serum NO 24 hours postop. In other words, at 24 hours postop, subjects who developed AF exhibit a negative change in serum NO that is about 58% more than that of subjects who do not develop AF.

EXEMPLARY EMBODIMENTS

The following methods are exemplary and are not intended to further limit the scope of the claims.

Method 1. A method of diagnosing a subject as having or likely to develop a postoperative complication after an operation, which comprises diagnosing the subject as having or likely to develop the postoperative complication where the subject's serum nitric oxide level, at 24 hours after the operation, is at least about 40% less than the subject's serum nitric oxide level prior to the operation.

Method 2. A method of diagnosing a subject as having or likely to develop a postoperative complication after an operation, which comprises diagnosing the subject as having or likely to develop the postoperative complication where, at 24 hours after the operation, the subject exhibits a negative change in serum nitric oxide that is at least about 28% more than that of a normal control.

Method 3. A method of diagnosing a subject as having or likely to develop a postoperative complication after an operation, which comprises diagnosing the subject as having or likely to develop the postoperative complication where the subject's serum nitric oxide level, at 24 hours after the operation, is about 40-45% less than the subject's serum nitric oxide level prior to the operation.

Method 4. A method of diagnosing a subject as having or likely to develop a postoperative complication after an operation, which comprises diagnosing the subject as having or likely to develop the postoperative complication where, at 24 hours postop, the subject exhibits a negative change in serum nitric oxide that is about 28-53% more than that of the normal control.

Method 5. A method of diagnosing a subject as having or likely to develop a postoperative complication after an operation, which comprises diagnosing the subject as having or likely to develop a postoperative complication where the subject's serum nitric oxide level, at 24 hours after the operation, is about 55-60% less than the subject's serum nitric oxide level prior to the operation.

Method 6. A method of diagnosing a subject as having or likely to develop a postoperative complication after an operation, which comprises diagnosing the subject as having or likely to develop the postoperative complication where, at 24 hours postop, the subject exhibits a negative change in serum nitric oxide that is about 64-67% more than that of the normal control.

Method 7A. A method of diagnosing a subject as having or likely to develop atrial fibrillation after an operation, which comprises diagnosing the subject as having or likely to develop atrial fibrillation where, at 24 hours after the operation, the subject exhibits a negative change in serum nitric oxide that is at least about 28% more than that of a normal control.

Method 7B. A method of diagnosing a subject as having or likely to develop atrial fibrillation after an operation, which comprises diagnosing the subject as having or likely to develop atrial fibrillation where, at 24 hours postop, the subject exhibits a negative change in serum nitric oxide that is about 28-53% more than that of the normal control.

Method 8A. A method of diagnosing a subject as having or likely to develop acute kidney injury after an operation, which comprises diagnosing the subject as having or likely to develop acute kidney injury where the subject's serum nitric oxide level, at 24 hours after the operation, is about 40-45% less than the subject's serum nitric oxide level prior to the operation.

Method 8B. A method of diagnosing a subject as having or likely to develop acute kidney injury after an operation, which comprises diagnosing the subject as having or likely to develop acute kidney injury where the subject's serum nitric oxide level, at 24 hours after the operation, is about 55-60% less than the subject's serum nitric oxide level prior to the operation.

In some embodiments of any one of the Methods 1-8B above, the operation is cardiac surgery. In some embodiments of any one of the Methods 1-8B above, the operation is cardiac surgery with cardiopulmonary bypass. In some embodiments of any one of the Methods 1-8B above, the method further comprises obtaining a blood sample from the subject and measuring the amount of nitric oxide in the sample using a detectable label added thereto. In some embodiments of any one of the Methods 1-8B above, the method further comprises calculating the difference between the amount of serum nitric oxide in a first blood sample obtained from the subject before the operation and the amount of serum nitric oxide in a second blood sample obtained from the subject about 24 hours after the operation. In some embodiments of any one of the Methods 1-8B above, the blood sample is a serum sample. In some embodiments of any one of the Methods 1-8B above, the method further comprises treating the subject for the postoperative complication where the subject is diagnosed as having the postoperative complication. In some embodiments of any one of the Methods 1-8B above, the subject is not treated for the postoperative complication where the subject is diagnosed as not having or not likely to develop the postoperative complication.

All scientific and technical terms used in this application have meanings commonly used in the art unless otherwise specified.

As used herein, the term "subject" includes humans and non-human animals. The term "non-human animal" includes all vertebrates, e.g., mammals and non-mammals, such as non-human primates, horses, sheep, dogs, cows, pigs, chickens, and other veterinary subjects and test animals.

The use of the singular can include the plural unless specifically stated otherwise. As used in the specification and the appended claims, the singular forms "a", "an", and "the" can include plural referents unless the context clearly dictates otherwise. The use of "or" can mean "and/or" unless stated otherwise. As used herein, "and/or" means "and" or "or". For example, "A and/or B" means "A, B, or both A and B" and "A, B, C, and/or D" means "A, B, C, D, or a combination thereof" and said "combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method of treating a subject after having had an operation, which comprises administering to the subject a pharmacologic agent known to treat atrial fibrillation and/or subjecting the subject to atrial pacing protocols where, at 24 hours postop, the subject exhibits a negative change in serum nitrogen oxide concentration that is at least about 28% more than the average percent decrease exhibited by normal control subjects.

2. The method according to claim 1, which further comprises optimizing the fluid status and correcting fluid volume deficits in the subject to maintain a mean blood pressure of greater than 65 mmHg and central venous pressure of greater than 8-12 mmHg in the subject and/or reducing dosages of nephrotoxic medications administered to the subject where, at 24 hours postop, the subject exhibits a negative change in serum nitrogen oxide concentration that is about 64-67% more than the average percent decrease exhibited by normal control subjects.

3. The method according to claim 1, wherein the percent decrease is about 28-58% more than the average percent decrease exhibited by normal control subjects.

4. The method according to claim 1, wherein the subject is treated before atrial fibrillation occurs.

5. The method according to claim 2, wherein the subject is treated before acute kidney injury occurs.

6. The method according to claim 1, wherein the operation is cardiac surgery.

7. The method according to claim 1, wherein the operation is cardiac surgery with cardiopulmonary bypass.

8. A method of treating a subject after having had an operation, which comprises administering to the subject a pharmacologic agent known to treat atrial fibrillation and/or subjecting the subject to atrial pacing protocols where, at 24 hours postop, the subject exhibits at least about a 40% decrease in serum nitric oxide concentration.

9. The method according to claim 8, wherein the percent decrease is about 28-58% more than the average percent decrease exhibited by normal control subjects.

10. The method according to claim 8, wherein the subject is treated before atrial fibrillation occurs.

11. The method according to claim 8, wherein the operation is cardiac surgery.

12. The method according to claim 8, wherein the operation is cardiac surgery with cardiopulmonary bypass.

13. A method of treating a subject after having had an operation, which comprises optimizing the fluid status and correcting fluid volume deficits in the subject to maintain a mean blood pressure of greater than 65 mmHg and central venous pressure of greater than 8-12 mmHg in the subject and/or reducing dosages of nephrotoxic medications administered to the subject where, at 24 hours postop, the subject exhibits (a) a negative change in serum nitrogen oxide concentration that is about 64-67% more than the average percent decrease exhibited by normal control subjects, or (b) about a 55-60% decrease in serum nitric oxide concentration.

14. The method according to claim 13, wherein the subject is treated before acute kidney injury occurs.

15. The method according to claim 13, wherein the operation is cardiac surgery.

16. The method according to claim 13, wherein the operation is cardiac surgery with cardiopulmonary bypass.

\* \* \* \* \*